United States Patent
Heffington

(10) Patent No.: US 9,332,793 B2
(45) Date of Patent: May 10, 2016

(54) EAR PROTECTION DEVICE FOR ATHLETES

(71) Applicant: Chris Heffington, Folsom, CA (US)

(72) Inventor: Chris Heffington, Folsom, CA (US)

(73) Assignee: Chris Heffington, Folsom, CA (US)

( * ) Notice: Subject to any disclaimer, the term of this patent is extended or adjusted under 35 U.S.C. 154(b) by 0 days.

(21) Appl. No.: 14/644,078

(22) Filed: Mar. 10, 2015

(65) Prior Publication Data

US 2015/0181990 A1      Jul. 2, 2015

Related U.S. Application Data

(63) Continuation-in-part of application No. 13/919,570, filed on Jun. 17, 2013, which is a continuation of application No. 13/735,158, filed on Jan. 7, 2013, now Pat. No. 8,484,993.

(60) Provisional application No. 61/950,833, filed on Mar. 10, 2014, provisional application No. 61/631,850, filed on Jan. 13, 2012.

(51) Int. Cl.
| | |
|---|---|
| *A44C 7/00* | (2006.01) |
| *A41F 1/00* | (2006.01) |
| *A41D 13/05* | (2006.01) |
| *A61F 11/14* | (2006.01) |

(52) U.S. Cl.
CPC ............... *A41D 13/05* (2013.01); *A44C 7/006* (2013.01); *A61F 11/14* (2013.01); *Y10T 24/1391* (2015.01); *Y10T 24/4447* (2015.01); *Y10T 24/44462* (2015.01)

(58) Field of Classification Search
None
See application file for complete search history.

(56) References Cited

U.S. PATENT DOCUMENTS

| | | | |
|---|---|---|---|
| 1,216,531 | A | 2/1917 | Wolf |
| 4,643,181 | A | 2/1987 | Brown |
| 5,035,123 | A | 7/1991 | Kogen |
| 5,444,994 | A | 8/1995 | Poorting et al. |
| 5,743,113 | A | 4/1998 | Kogen |
| 6,003,333 | A | 12/1999 | Stevens |
| 6,263,703 | B1 | 7/2001 | Kenney |
| 7,111,370 | B2 | 9/2006 | Daniel |
| 7,850,702 | B2 | 12/2010 | Sorribes |
| 8,113,208 | B2 | 2/2012 | Chaisson et al. |

OTHER PUBLICATIONS

Lavinder, Jack W., "Office Action re U.S. Appl. No. 13/735,158", Apr. 26, 2013, pp. 17, Published in: US.
Gruber, Stephen S., "Response to Office Action re U.S. Appl. No. 13/735,158", May 15, 2013, p. 8 Published in: US.

*Primary Examiner* — Jack W Lavinder
(74) *Attorney, Agent, or Firm* — Neugeboren O'Dowd PC

(57) ABSTRACT

This disclosure describes systems, methods, and apparatus for an earring safety device that can be clipped to an ear enveloping an earring so as to protect the ear and the wearer's head from the earring during fast-paced activities. The earring safety device can enable athletes, manufacturing workers, and others to participate in contact sports or dangerous craft without removing the earring, especially where sport or labor rules would otherwise preclude the athlete or worker from competing or working. The earring safety device can also protect the wearer from snagging the earring during high-intensity activities and dangerous workplace activities. The protection also protects the athlete, worker, or other person from injury due to impacts made to the earring.

20 Claims, 15 Drawing Sheets

FRONT

BACK

FRONT

BACK

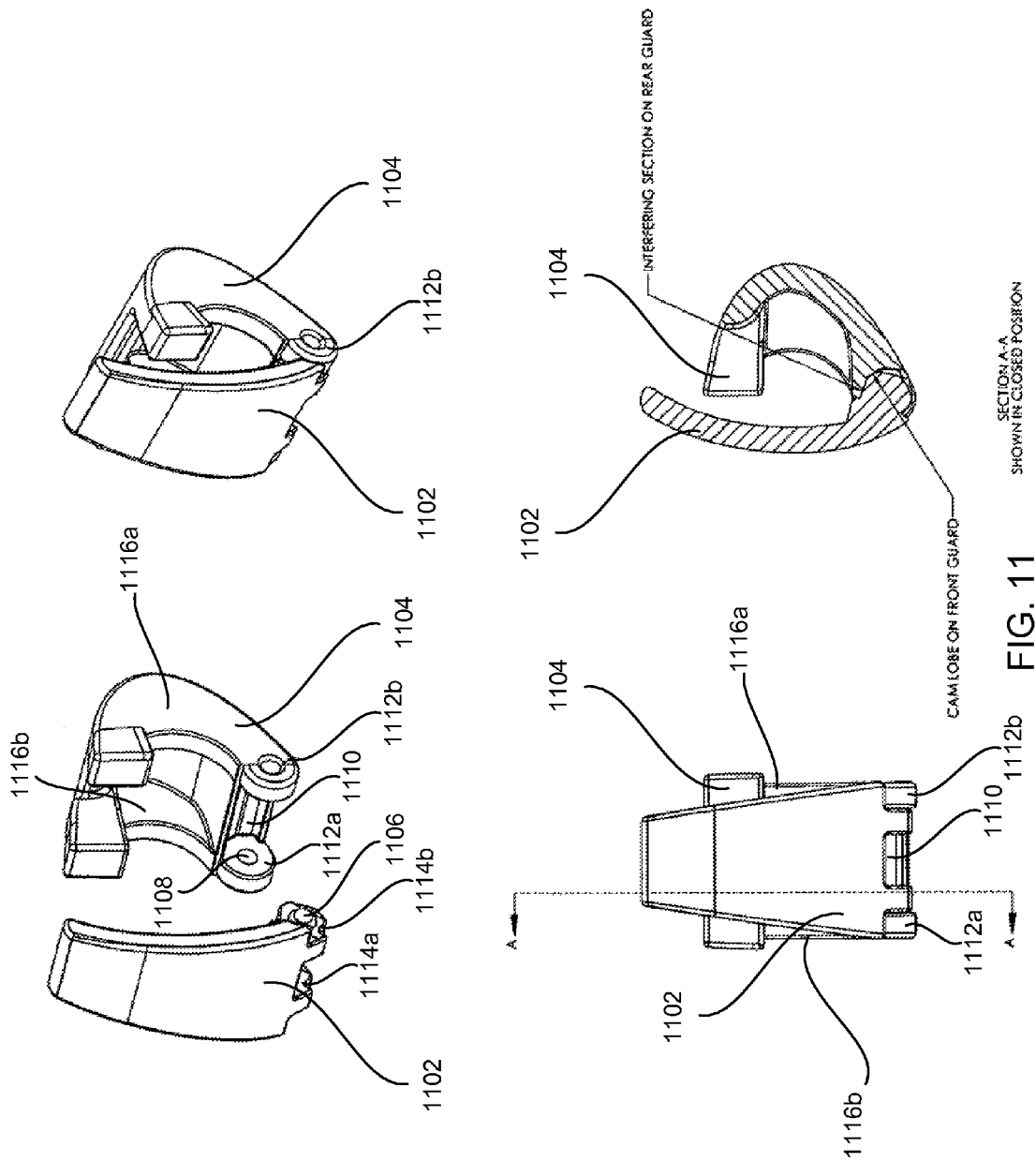

EAR PROTECTION DEVICE FOR ATHLETES

RELATED CASES AND PRIORITY

This application claims the benefit of Provisional U.S. Patent Application No. 61/950,833, entitled "EAR PROTECTION DEVICE FOR ATHLETES," filed on Mar. 10, 2014. This application is also a Continuation-In-Part of U.S. patent application Ser. No. 13/919,570, entitled "EAR PROTECTION DEVICE FOR ATHLETES," filed Jun. 17, 2013, which is a Continuation of U.S. application Ser. No. 13/735,158, now U.S. Pat. No. 8,484,993, entitled "EAR PROTECTION DEVICE FOR ATHLETES," filed Jan. 7, 2013, and this application claims the benefit of Provisional U.S. Patent Application No. 61/631,850, entitled "EAR PROTECTION DEVICE FOR ATHLETES," filed on Jan. 13, 2012, the details of these applications are incorporated by reference into the present application in their entirety

FIELD OF THE DISCLOSURE

This invention relates to methods and apparatus for protecting ears, and in particular, to methods and apparatus for protecting pierced ears and adjacent tissue from physical injury during sporting or other fast-paced activities.

BACKGROUND

Participation in youth sports while wearing one or more earrings or ear piercings generates a host of safety issues that are often addressed by rules and policies. Objects that strike the ear when an earring is in place can cause the backing to strike the skull causing discomfort and/or injury. Earrings and piercings of the ear can also snag on clothing or equipment. Such injuries have predominantly been seen in sports such as soccer, lacrosse, field hockey, softball and basketball, to name a few. In most cases rules require a player to remove his/her earring prior to the start of play. This can present a difficult decision for some athletes with newly pierced ears because they have been told that if they remove the earrings from the piercing that the hole will close up. This can lead to players choosing not to play rather than choosing to remove their earring(s). Some leagues allow a player to cover the earring or ear piercing with tape such as athletic tape. However, the athletic tape provides little to no protection and has significant aesthetic drawbacks.

Other solutions have considered medical adhesive bandages, which may have a thicker, padded portion that is centrally located on the bandage, however the padded portion typically does not cover all portions of the ear and the earring that need to be protected. For instance if the padded portion covers the earring on the front of the earlobe, then only a thin adhesive layer typically protects the back of the earring (or the earring backing). Adhesive bandages are also designed to be substantially flush with the surface that they are covering. Earrings present sharp protruding edges, and anything but the subtle curves that bandages typically affix to on human flesh. As such, adhesive bandages are awkward to affix to both the earlobe and the earring. Additionally, even this added thickness may not be sufficient to prevent injury to the head or neck if the ball hits the ear shoving the back portion or earring backing into the athletes head or neck. Athletes, especially younger ones, can also be self-conscious of wearing "Band-Aids" on their ears.

A variety of solutions propose the use of some sort of adhesive to secure a protecting device or material to the ear. However, these solutions are one-time use solutions.

Yet further solutions have considered clip on protective earrings for attachment to a user's ear including a pair of pivotally-coupled clamshell protectors. However, the clamshell design allows an earring backing to move in various directions relative to the protector, which can lead to discomfort. Furthermore, a clamshell shape often has a shallow depth making it more likely that an earring backing will be pressured by the clamshell protector into the ear thus further causing discomfort. Additionally, a clamshell design distributes a pressure of the clamping around a narrow outer rim or circumference of the clamshell thus applying focused pressure on the ear.

There is therefore a need in the art for a reusable protective device offering greater protection than athletic tape or bandages, offering comfort, and being acceptable by a variety of youth sports organizers.

SUMMARY OF THE DISCLOSURE

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

Some embodiments of the disclosure may be characterized as an earring safety device arranged over an earring of an ear. The device can include a back arced portion, right and left flanges, and a tension mechanism. The front face can be configured for proximal arrangement to a front of the earring so as to protect the earring from external impacts, a top curved portion of the front face arranged so as to hook around an antitragus or helix of the ear and assist in holding the earring safety device onto the ear. The back arced portion can be pivotally coupled to the front portion. The right and left flanges can extend from the back arced portion towards the front face and can be configured to restrict movement of an earring backing from lateral motion. The tension mechanism can be coupled to the front face and the back arced portion so that the front face and the back arced portion are rotatably pressed towards each other, and are configured to press a portion of the ear between the back arced portion and the front face to decrease movement between the earring safety device, the earring, and the ear.

Other embodiments of the disclosure may also be characterized as an earring safety device arranged over an earring of an ear so as to prevent external contact with the earring. The earring safety device can comprise a front face, a back arced portion, and a tension mechanism. The front face can be configured to be arranged proximal to a front face of the earring. The back arced portion can be rotatably coupled to the front portion via an axis of rotation that intersects a bottom of the front face and a bottom of the back arced portion, the back arced portion having a concave region facing an inner surface of the front face. The tension mechanism can overlap the axis of rotation and couple to the front face and the back arced portion, the tension mechanism applying a force to the front face and the back arced portion configured to cause the inner surface of the front face to rotate around the axis of rotation towards the back arced portion.

Other embodiments of the disclosure can be characterized as a method of protection against bodily harm from an earring fixed to an ear. The method can comprise rotatably separating a back arced portion of an earring safety device from a front face of the earring safety device creating a gap between a top of the back arced portion and an inner surface of the front face. The method can further comprise fitting an edge of the ear through the gap so that the earring safety device envelopes the earring fixed to the ear. The method can also comprise releasing the back arced portion and the front face so that a tension mechanism of the earring safety device rotatably closes the gap and clamps the earring safety device to the edge of the ear.

Another aspect of the disclosure is an earring safety device arranged over an earring of an ear. The earring safety device can include a front guard, rear guard, a camming lobe, and right and left flanges. The front guard can be configured for proximal arrangement to a front of the earring so as to protect the earring from external impacts, a top curved portion of the front guard arranged so as to hook around an antitragus or helix of an ear and assist in holding the earring safety device onto the ear. The rear guard can be pivotally coupled to the front guard. The front guard can be tapered such that a bottom of the front guard is wider than a top of the front guard. The camming lobe can be shaped to provide a first resistance to rotation of the front and rear guards when the front and rear guards are rotated between open and closed positions, and to provide at least a second resistance to rotation of the front and rear guards relative to each other when the front and rear guards are in the open or closed positions, the first resistance being greater than the second resistance. The right and left flanges can be of the rear guard and can extend from the rear guard towards the front guard and configured to restrict movement of an earring backing of the earring from lateral motion. This earring safety device can also include an earring release slot in the rear guard that enables the earring to slide through the earring safety device without damaging the ear when the earring safety device is forcibly removed from the ear.

Yet another aspect of the disclosure is an earring safety device arranged over an earring of an ear. The earring safety device can include a front guard, a rear guard, and a camming lobe of the rear guard.

BRIEF DESCRIPTION OF THE DRAWINGS

Various objects, advantages and a more complete understanding of the present invention are apparent and more readily appreciated by referring to the following detailed description and to the appended claims when taken in conjunction with the accompanying drawings:

FIG. 11 illustrates an embodiment of an ear protection device using a cam design;

DETAILED DESCRIPTION

The present disclosure relates generally to bodily protection and more particularly to apparatus and methods for preventing bodily injury from earrings worn during sports, manufacturing, or other activities.

The word "exemplary" is used herein to mean "serving as an example, instance, or illustration." Any embodiment described herein as "exemplary" is not necessarily to be construed as preferred or advantageous over other embodiments.

Prior solutions have been held back by lack of comfort, insufficient product strength, and movement of the device relative to the ear and the earring, insufficient protection from all sides, and inability to be used on other than the earlobe of the ear. The herein disclosed earring safety device uses a novel shape and clamping mechanism to distribute pressure across the ear and to greatly improve the comfort of the device. Further, the shape of the device prevents substantial movement of the earring or ear relative to the device thus improving comfort and safety. In contrast, solutions known in the art, such as clamshell devices or adhesive type products allow the earring backing to move side to side up to 180 degrees which could cause discomfort. The device also provides a full six sides of protection and is configured for use on various portions of the ear including the helix.

Figure 1:
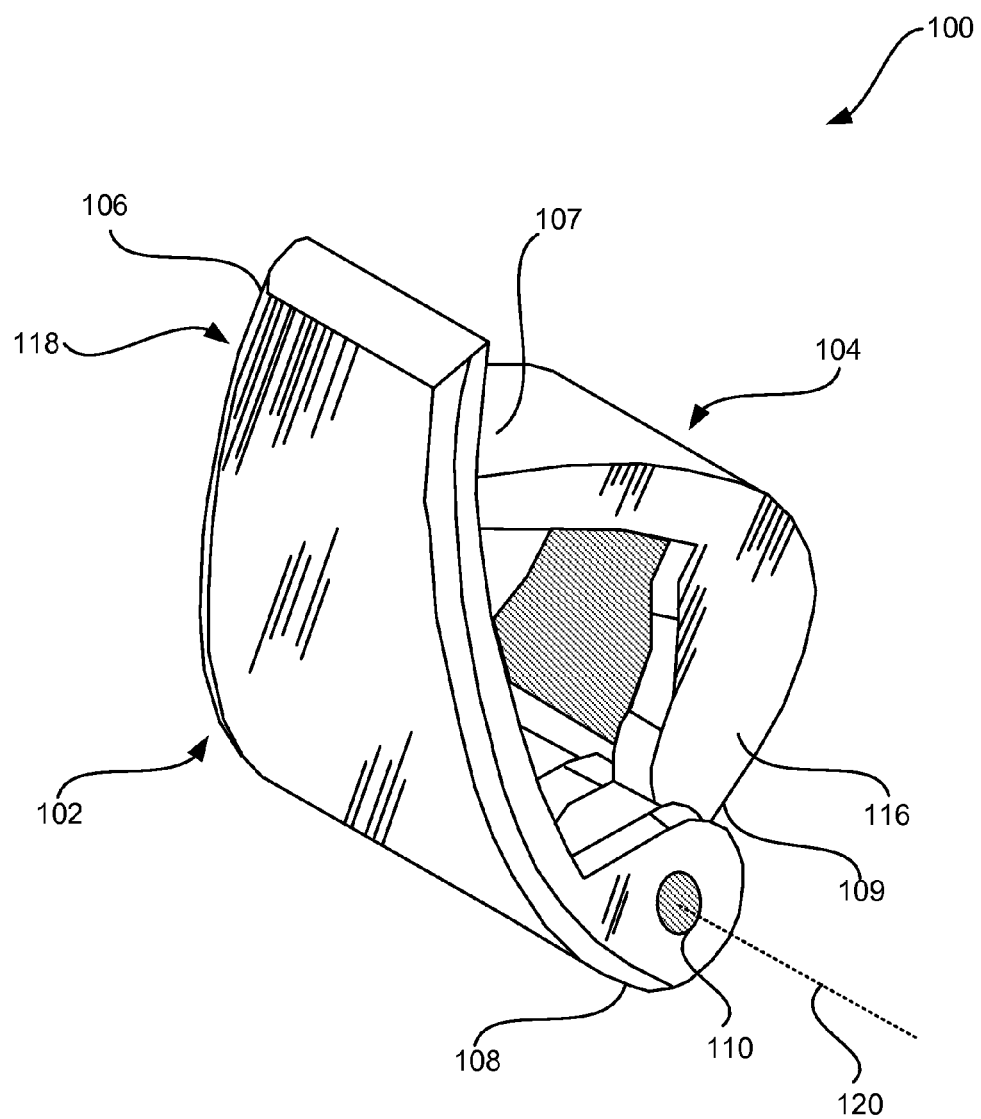
FIG. 1 illustrates a three-quarter view of an earring safety device.

FIG. 1 illustrates a three-quarter view of an earring safety device. The earring safety device 100 includes a front face 102 and a back arced portion 104. The front face 102 and the back arced portion 104 are coupled via a tension mechanism 110 that overlaps an axis of rotation 120 passing through a bottom 108 of the front face 102 and a bottom 109 of the back arced portion 104. The tension mechanism 110 causes the front face 102 and the back arced portion 104 to be pivotally forced towards each other around the axis of rotation 120. The earring safety device 100 can also include flanges 116 protruding from the back arced portion 104 towards the front face 102. The combination of the curvature of the back arced portion 104 and the flanges 116 creates a concave region 250 (see FIG. 2B) suitable for accepting an earring backing. Flanges 116 act as "guard rails" limiting the movement of the earring backing, which ensures the earring backing is covered at all times. The front face 102 has less curvature (or can be flat) than the back arced portion 104, and is therefore well-suited to press protect a front portion of an earring and a front of the earlobe or helix, where a front portion of an earring typically protrudes less than the earring backing.

The front face 102 can be tapered such that the bottom 108 is wider than the top 106. The back arced portion 104 can also be tapered such that the bottom 109 of the back arced portion 104 is wider than a top 107 portion of the back arced portion 104. This tapering is more clearly seen in FIGS. 2A and 2B.

Figure 2A:
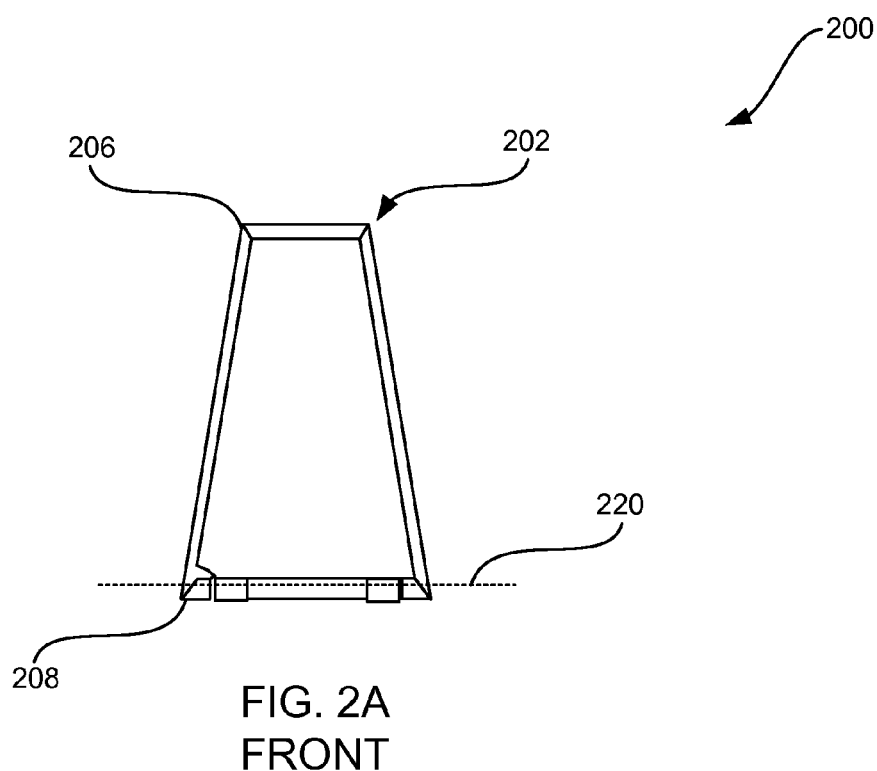
FIG. 2A shows a front of the earring safety device 200.

FIG. 2A shows a front of the earring safety device 200. Only the front face 202 is visible here and the taper is clearly visible with the top 206 being narrower than the bottom 208.

Figure 2B:
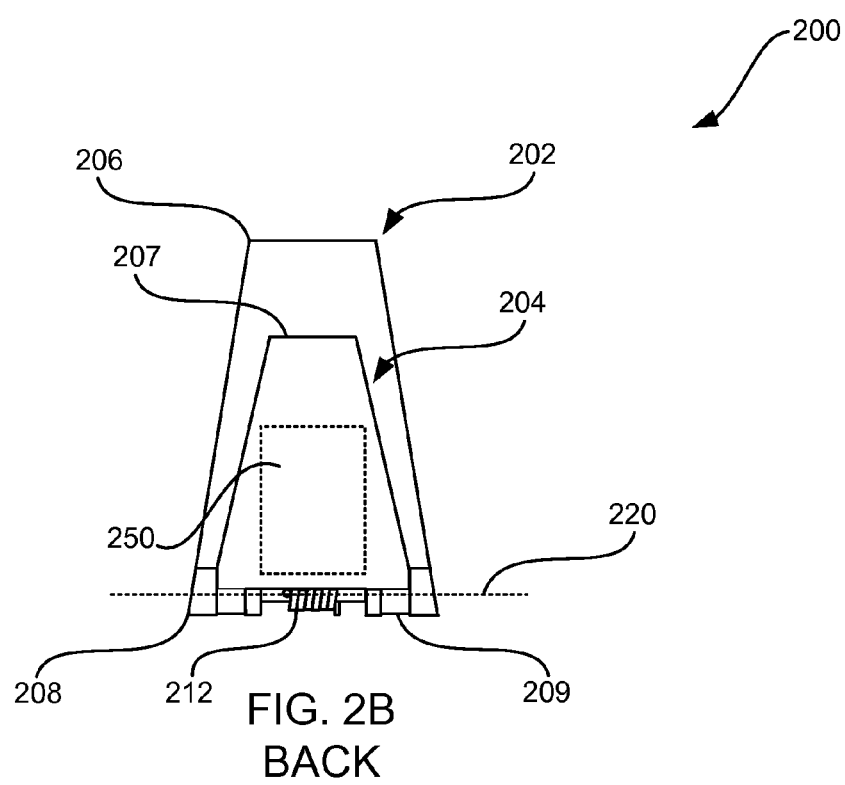
FIG. 2B shows a back of the earring safety device 200.

FIG. 2B shows a back of the earring safety device 200. Here both the back arced portion 204 and parts of the front face 202 can be seen. The top 206 of the front face 202 is narrower than the bottom 208 of the front face 202 while a top 207 of the back arced portion 204 is narrower than a bottom 209 of the rear arched portion 204. The illustrated taper is not limiting, and any taper angle can be used. Also, the taper of the front face 202 and the back arced portion 204 can differ, as illustrated. There is also no requirement that the taper be linear.

Dashed lines in FIG. 2B indicate an outline of the concave region 250 in which the earring backing can rest and thus reduce movement of the earring relative to the earring safety device 200. Furthermore, the concave region 250 can be large enough to accept an entire earring backing such that the earring safety device is not placing pressure on the earring backing unlike the way that clamshell or adhesive design do.

The tension mechanism 110 of FIG. 1 is illustrated in FIGS. 2A and 2B as a coiled spring 212 around a post, where the spring 212 creates a rotational force around the axis of rotation 220. This rotational force presses the front face 202 and the back arced portion 204 together at a top 207 of the back arced portion 204 and at a location in the upper half of the front face 202. In other embodiments, other tension mechanisms can be used—for instance, other types of springs or materials with elastic qualities can be used. In one embodiment, a stiff rubber or rubber-like material can wrap around the axis 220 or be a part of the axis 220 and twisting of this material can create the tension. In one embodiment, the tension mechanism 110 can be partially or wholly covered or enveloped. For instance, given a coiled spring as the tension mechanism, a plastic enclosure may envelope the coiled spring to help prevent an earring from snagging on any exposed portions of the coiled spring.

Figure 3:
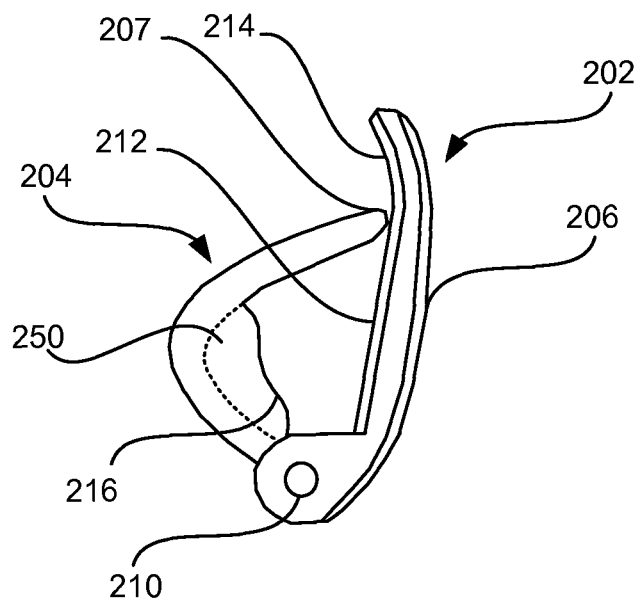
FIG. 3 illustrates a side view of an embodiment of an earring safety device.

FIG. 3 illustrates a side view of an embodiment of an earring safety device. The front face 202 can be seen to be coupled to the back arced portion 204 via a tension mechanism 210 which causes a top 207 of the back arced portion 204 to rotatably press against an inner face 212 of the front face 202. In this fashion, the front face 202 and the back arced portion 204 can rotatably press against each other clamping a portion of an earlobe between them. One of the flanges 216 can be seen to extend from the back arced portion 204 so as to form one side of the concave region 250. Although only one of the two flanges 216 is visible in FIG. 3, the following will refer to both flanges 216 as these features are equally applicable to both flanges 216.

An inside face 212 of the front face 202 is illustrated as being substantially flat. However, in other embodiments, greater curvature than that shown is possible. Both a front of the earring and portions of the earlobe, helix, or other parts of the ear can be pressed against this inner face 212 when in use.

A top curved portion 214 of the front face 202 has curvature or an angle enabling the top curved portion 214 to hook around an antitragus or helix of an ear. The angle and length of the top curved portion 214 can be tailored for different parts of the ear or can be generalized so as to fit various portions of the ear. The illustrated shape, angle, and dimensions of the top curved portion 214 are thus not limiting.

The flanges 216 can be shaped so as to fit a back of the earlobe, helix of the ear, or some other part of the ear. Alternatively, the flanges 216 can be shaped so as to reduce or distribute a pressure on the back of the earlobe, helix of the ear, or some other part of the ear. The illustrated flanges 216 extend partway to an inner surface 212 of the front face 202 so that there is room for the earlobe, helix, or other portion of the ear between the back arced portion 204 and the front face 202. An angle of the flanges 216 relative to the back arced portion 204 as well as a thickness of the flanges 216 can vary as long as the concave region 250 maintains sufficient volume to accept an earring backing.

Figure 9:
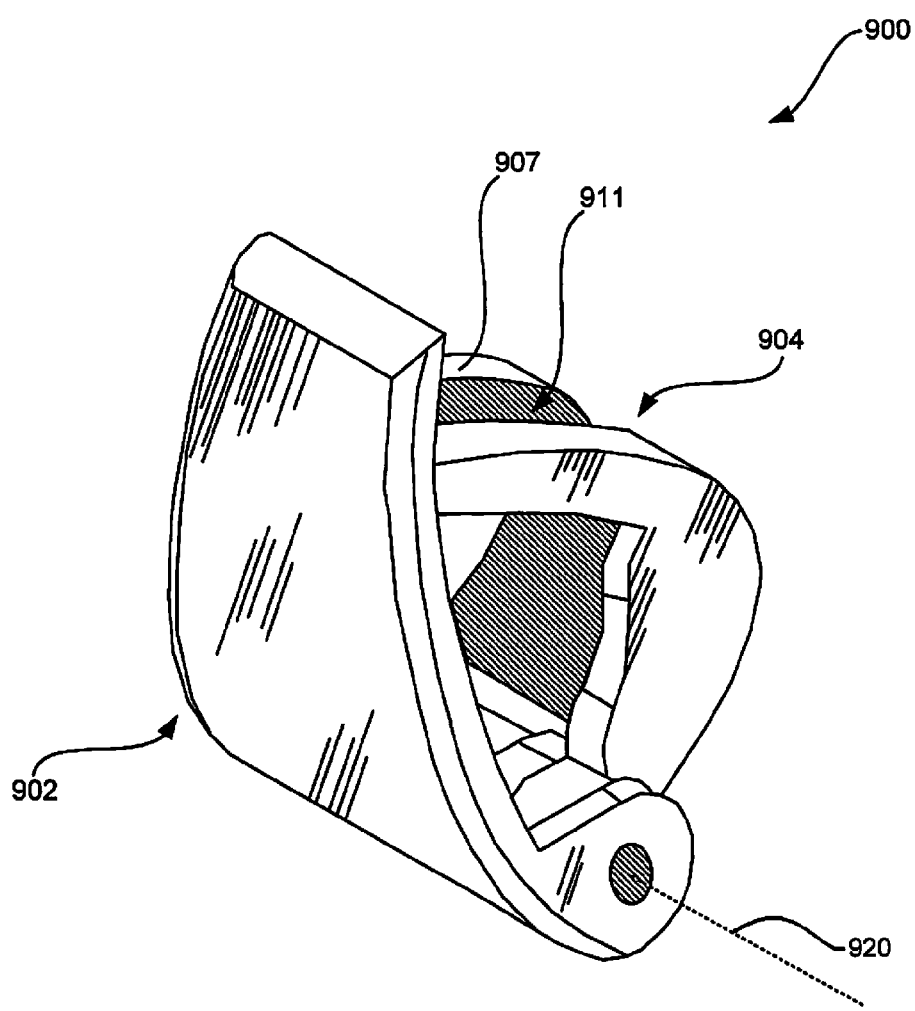
FIG. 9 illustrates a three-quarter view of another earring safety device.

If the earring safety device 200 were to be pulled from an ear, there is the possibility of injury and the device 200 might pull the earring out of the ear via tearing through skin. One solution is the addition of an earring release slot 911 as illustrated in FIG. 9. The earring release slot 911 can be cut completely through the back arced portion 904 so that an earring can pass through the earring release slot 911 if the earring safety device 900 is pulled and the back arced portion 904 does not open relative to the front face 902. The earring safety device 900 can open and close by means of the back arced portion 904 and the front face 902 rotating relative to each other about an axis of rotation 920. FIG. 9 also shows the back arced portion 904 having a top 907.

Figure 10A:
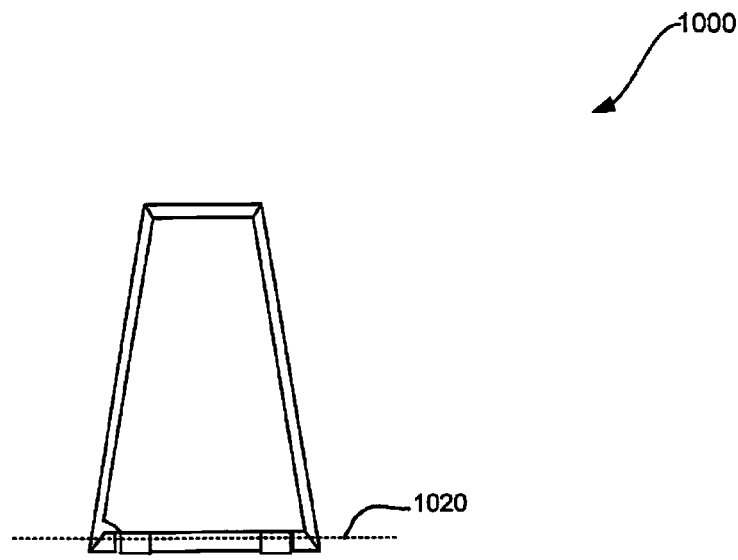
FIG. 10A shows a front of the earring safety device with an earring release slot as was illustrated in FIG. 9.
Figure 10B:
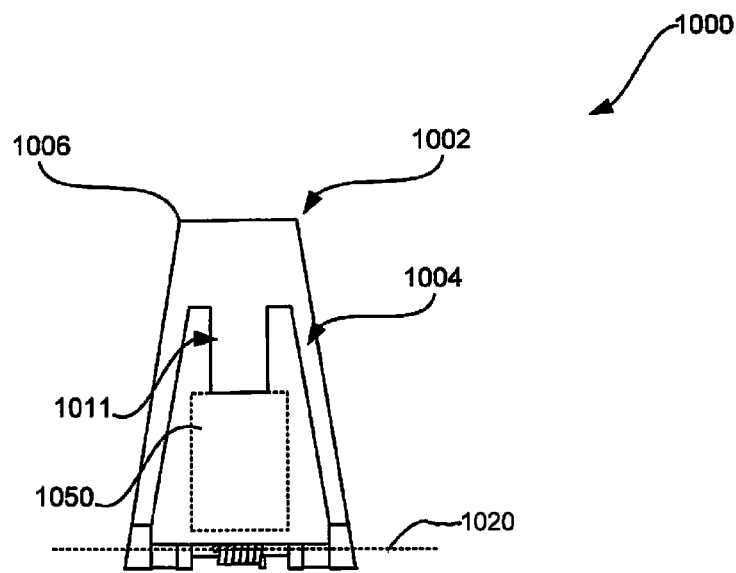
FIG. 10B shows a back of the earring safety device with the earring release slot illustrated in FIG. 9.

FIG. 10A shows a front of the earring safety device 91000, and while FIG. 10B shows a back of the earring safety device 91000. A concave region 1050 is seen in a back arced portion 1004 where the earring backing can rest and thus reduce movement of the earring relative to the earring safety device. In the event that the earring safety device 1000 is pulled from the ear, an earring release slot 1011 is arranged through the back arced portion 1004 to allow the earring to slide through the earring safety device 1000. FIGS. 10A and 10B also show the axis, 1020.

The earring release slot 1011 is illustrated as abutting a top of the concave portion 1050, however in other embodiments, the earring release slot 1011 can be cut into the concave portion 1050 or can be short enough that it does not abut a top of the concave portion 1050. The earring safety device 1000 also includes a front face 1002 having a top 1006.

Figure 4:
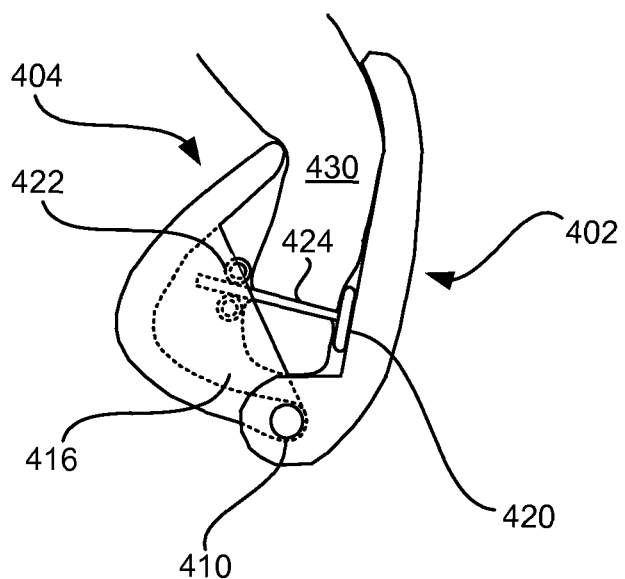
FIG. 4 illustrates a side view of an embodiment of an earring safety device coupled to a pierced ear.

FIG. 4 illustrates a side view of an embodiment of an earring safety device coupled to a pierced ear. An earlobe 430 can be seen to have an earring passing through it, the earring having a front portion 420, a rod 424, and an earring backing 422. Typically the rod 424 is permanently attached to the front portion 420 and these two pieces can be affixed to and removed from the earring backing 422.

A front face 402 of the earring safety device is coupled to a back arced portion 404 via a tension mechanism 410. The tension mechanism 410 can overlap an axis of rotation about which the back arced portion 404 and the front face 402 rotate. The tension mechanism 410 generates a force tending to force the back arced portion 404 to rotate towards the front face 402 until the two meet or until they clamp the earlobe 430 between them. The back arced portion 404 can be forcibly separated from the front face 402 forming a gap through which the earlobe 430 or some other edge portion of the ear can be passed through. The back arced portion 404 and the front face 402 can then be released, and the force generated by the tension mechanism 410 will cause the back arced portion 404 and the front face 402 to close on the earlobe 430 or other edge portion of the ear so as to clamp the earring safety device to the ear.

The flat angle of the front face 402 helps distribute the pressure that the back arced portion 404 places on the earlobe 430 (or other edge portion of the ear) thus improving the comfort and wearability of the earring safety device. For instance, were a clamshell shaped earring safety device used, the clamshell edges on both the back and the front halves would put great pressure on the earlobe and lead to discomfort.

The concave shape of the back arced portion 404 helps to accept the earring backing 422 of the earring. The flanges 416 help keep the earring from moving side to side and thereby create a concave region (e.g., concave region 25) around the earring backing 422 that help prevent it from moving. This enhances the stability of the entire earring and earlobe 430 within the earring safety device, thus improving comfort and decreasing the risk of injury.

The substantially flat shape of the front face 402 distributes pressure from impacts on the front of the earring 420 and on the front of the earlobe 430 or other edge portion of the ear. The back arced portion 404 protects the wearer's head and neck from the earring backing 422, where an unprotected earring backing 422 could be driven into the wearer's head and neck via impact on the front 420 of the earring from a ball, body, or other object. The back arced portion 404 provides not only a protective layer between the earring backing 422 and the wearer's skin, but also helps to distribute the force of such an impact via its curved shape. In some embodiments, padding or a softer material can be used where the back arced portion 404 and the front face 402 clamp the earlobe 430 via clamping pressure. For instance, a silicone layer could be applied to portions of the back arced portion 404 and portions of the front face 402 that often contact the earlobe 402.

Without protection, an earring has a risk of snagging which could cause extreme pain if not injury via tearing of the skin where the rod 424 passes through the earlobe 430 or other edge portion of the ear. However, the earring protection device envelopes the earring from all six directions of approach, thus reducing the risk of snagging. In the event that the earring safety device snags, the clamping method used is such that the earring safety device can be pulled from the ear without causing injury. In other words, the back arced portion 404 and the front face 402 may be forced apart as the earring safety device is pulled from the earlobe 430 or other edge portion of the ear. However, such release is easily accomplished without injury to the wearer or damage to the earring safety device.

The illustrated configuration and shape of the earring in FIG. 4 is illustrative only, and the earring safety device is equally capable of operation with various other forms and shapes of earrings.

Figure 5:
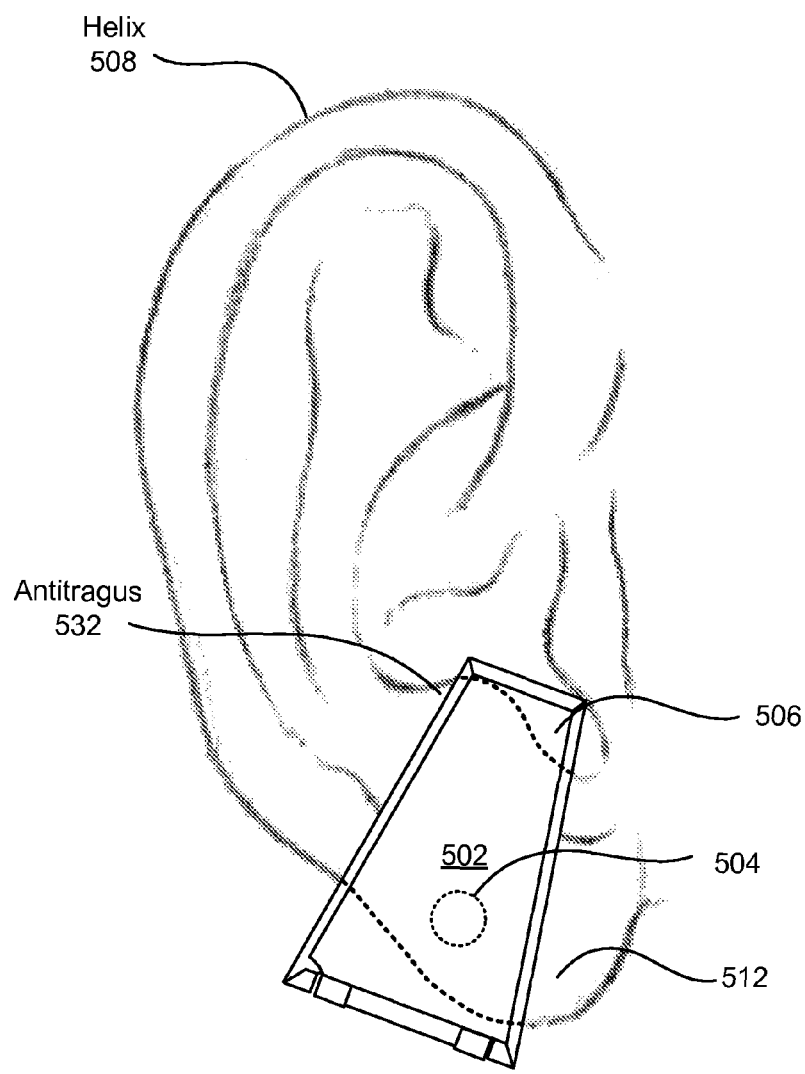
FIG. 5 illustrates an earring safety device arranged over an earlobe and antitragus of an ear.

FIG. 5 illustrates an earring safety device arranged over an earlobe and antitragus of an ear. The earring safety device 502 can latch onto the antitragus 532 of the ear with the back arced portion and the front face pinching the ear between them. The earring safety device 502 can be arranged to surround an earring 504, illustrated as a stud-type earring piercing the earlobe 512, although other earring types can also be enveloped in this way. A top curved portion 506 of the front face can be arranged so as to curve around a top of the antitragus 532 to help hold the earring safety device 502 in place. The earring safety device 502 has a great enough length that it can span from below the earlobe 512 to above a top edge of the antitragus 532. The taper from bottom to top helps the top curved portion 506 of the front face to curve around a top edge of the antitragus 532 while leaving a greater surface area lower down on the earlobe 512 to distribute the clasping pressure thus increasing comfort.

Figure 6:
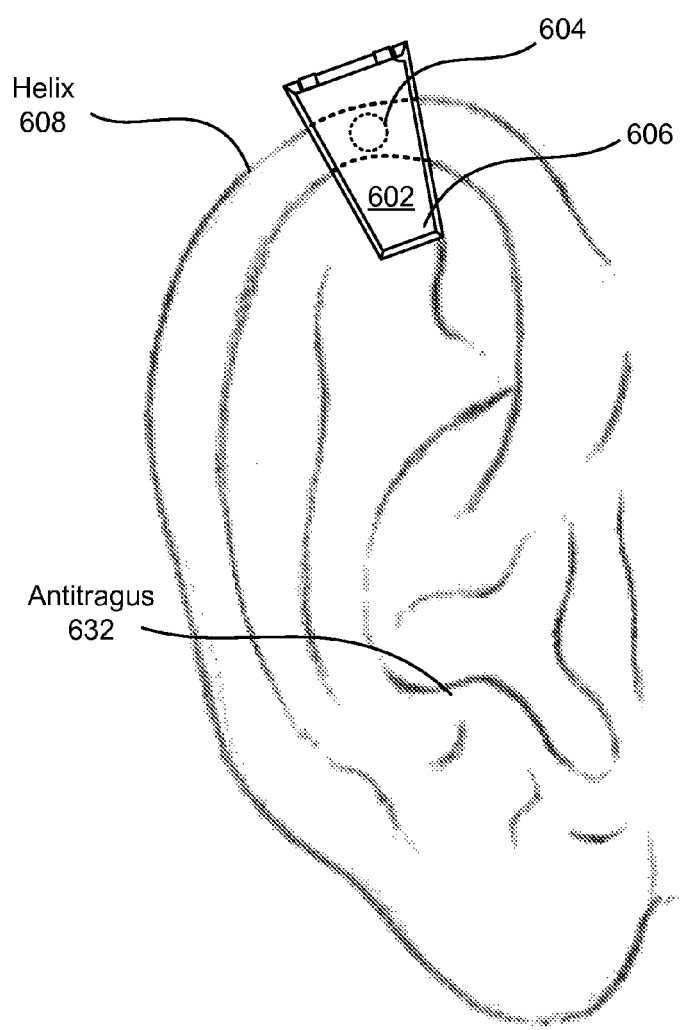
FIG. 6 illustrates an earring safety device arranged over an earring in a helix of an ear.

FIG. 6 illustrates an earring safety device arranged over an earring in a helix of an ear. In this illustration the earring safety device 602 is arranged so that the wider portion of the earring safety device 602 rests above the helix 608 while the narrower portion rests below the helix 608 thus enveloping an earring 604 that is fixed through the helix 608. In this case, a top curved portion 606 of the earring safety device is arranged so that it curves under the helix 608 to help hold the device 602 in place.

Because of the shape of the earring safety device 602, the earring 604 can be located on any part of the helix 608. The earring safety device 602 is thus not limited to the location or angular arrangement illustrated in FIG. 6.

Figure 7:
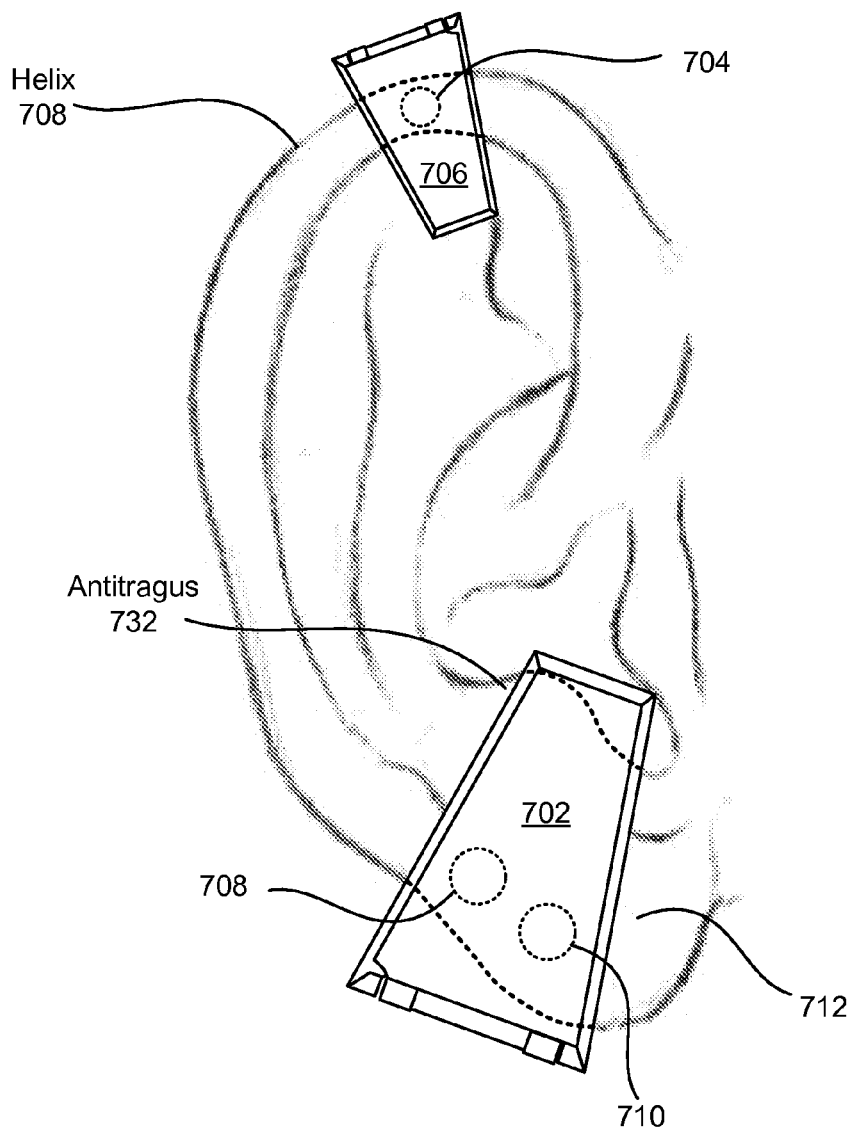
FIG. 7 illustrates an embodiment of two earring safety devices arranged on different portions of the ear.

FIG. 7 illustrates an embodiment of two earring safety devices arranged on different portions of the ear. Here, a first, and larger, earring safety device 702 envelopes two earrings 708 and 710 that are fixed in the earlobe 712. This earring safety device 702 may be wider than other embodiments so as to accommodate the two earrings 708 and 710. A second earring safety device 706 envelopes a third earring 704 fixed to the helix 708 of the ear. Because the second earring safety device 706 only has to accommodate a single earring 704, it can have smaller dimensions than the first earring safety device 702.

Figure 8:
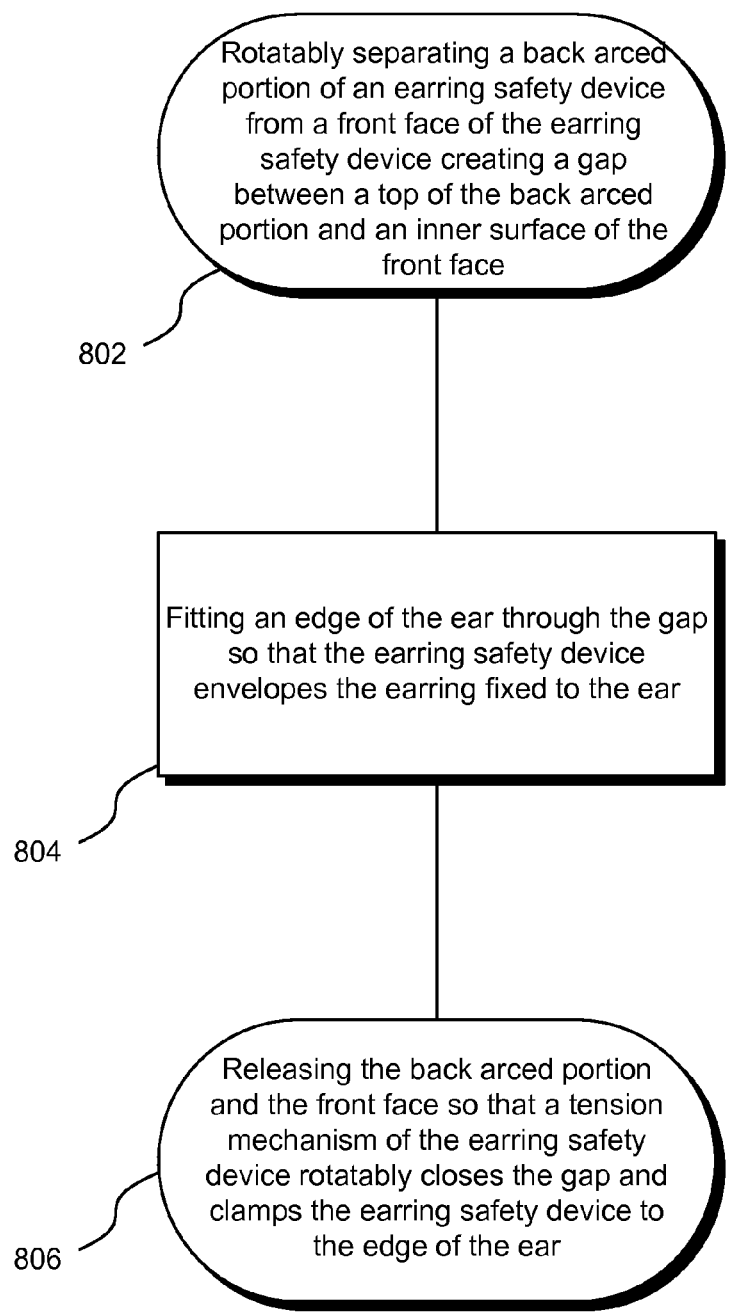
FIG. 8 illustrates a method of protection against bodily harm from an earring fixed to an ear.

FIG. 8 illustrates a method of protection against bodily harm from an earring fixed to an ear. The method includes rotatably separating a back arced portion of an earring safety device from a front face of the earring safety device creating a gap between a top of the back arced portion and an inner surface of the front face—otherwise referred to as a separating operation 802. The method further includes fitting an edge of the ear through the gap so that the earring safety device envelopes the earring fixed to the, which can be referred to as a fitting operation 804. The method still further includes releasing the back arced portion and the front face so that a tension mechanism of the earring safety device rotatably closes the gap and clamps the earring safety device to the edge of the ear. This final operation can be referred to as a releasing operation 806.

FIG. 11 illustrates an embodiment of an ear protection device using a cam design. The illustrated embodiment includes a front guard 1102 and a rear guard 1104 that snap together and rotate about an axis relative to each other. In this embodiment male portions 1106 on the front guard 1102 can snap into female portions 1108 on the rear guard 1104 thereby allowing the front guard 1102 and rear guard 1104 to rotate about an axis passing through the male and female portions 1106, 1108. For instance, the female portions 1108 can be embodied as spherical detents and the axis can pass through these spherical detents. In some cases the female portions 1108 can be indentations that pass only partly through the rear guard 1104, as illustrated, while in other instances they can be through holes that pass completely through the material of the rear guard 1104. While the illustrated embodiment shows the male portions 1106 being part of the front guard 1102 and the female portions 1108 being part of the rear guard 1104, in other embodiments these roles can be reversed.

The front guard 1102 can pivot up to 90° using an axis through the male and female portions 1106, 1108. The male portions 1106 can extend outward from tabs on either side of the front guard 1102 as shown. In some embodiments, these tabs can have a profile that is other than circular. For instance, the illustrated tabs have an irregular and angled shape. In other embodiments, a decreasing radius outline can be used.

In the illustrated embodiment, the rear guard 1104 includes a camming lobe 1110 that sits between two tabs 1112a, 1112b where the tabs 1112a, 1112b house the female portions 1108. The camming lobe 1110 is shaped to receive tabs 1114a, 1114b of the front guard 1102, and is shaped so that the tabs 1114a, 1114b of the front guard 1102 see a camming action as they rotate. For instance, the camming lobe 1110 and the tabs 1114a, 1114b of the front guard 1102 can be shaped so that a snug fit is achieved when the ear protection device is either in an open or closed position, but a friction or interference fit is seen in between these positions (e.g., when the front and rear guards 1102, 1104 are rotating between the open and closed positions). In other words, the front and rear guards 1102, 1104 see increasing friction and resistance as they close, but at a certain point the resistance slackens or terminates. Similarly, great force is required at first to rotate the front and rear guards 1102, 1104 into an open position, but once past a certain rotational angle, the front and rear guards 1102, 1104 easily continue to rotate. In this fashion, the ear protection device can stay in a closed position without the use of any springs or other tension mechanisms to hold the front and rear guards 1102, 1104 in a closed position. This camming action results in forces similar to the spring action of an over-center hinge reflex (e.g., see FIG. 10). Said another way, the front and rear guards 1102, 1104 can be rotated between open and closed positions, and the camming lobe 1110 can be shaped to provide a first resistance when the front and rear guards 1102, 1104 are rotated between these two positions. FIG. 11 shows the earring safety device in the closed position. The camming lobe 110 can provide at least a second resistance when the front and rear guards 1102, 1104 are in the open or closed positions, where the second resistance is less than the first resistance. In some embodiments, the camming lobe 110 can be shaped to provide a second resistance when the front and rear guards 1102, 1104 are in the open position and a third resistance when the front and rear guards 1102, 1104 are in the closed position. The second resistance can be greater than the third resistance, or the third resistance can be greater than the second resistance. In some embodiments, the first, second, and optionally the third resistance can be a byproduct of a friction or interference fit between the front and rear guards 1102, 1104. In some embodiments, the first and/or rear guards can flex when the front and rear guards 1102, 1104 are rotated between the closed and open positions, and this flexing acts like a spring force to provide resistance between the open and closed positions.

Figure 12:
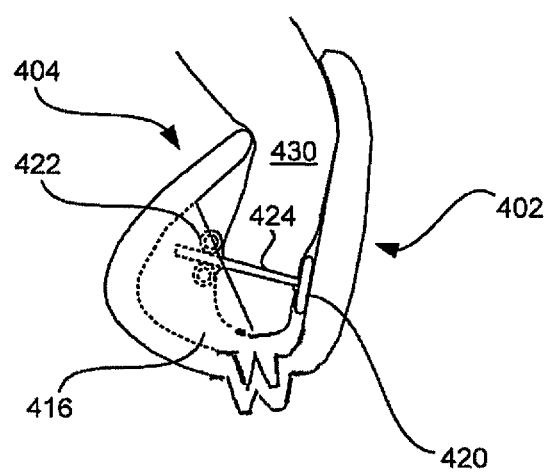
FIG. 12 illustrates an embodiment of an ear protection device using a first static spring design.
Figure 13:
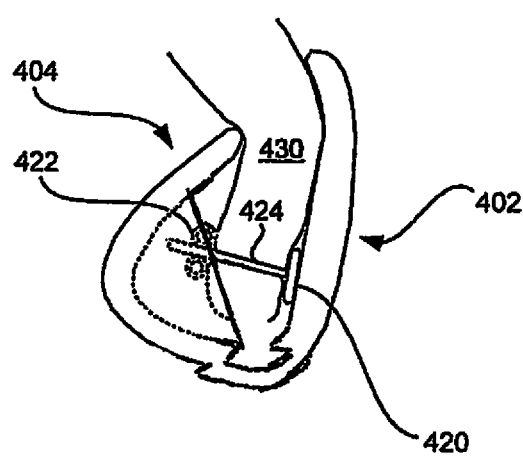
FIG. 13 illustrates an embodiment of an ear protection device using a second static spring design.

The earring safety device can further include left and right flanges 1116a, 1116b (as viewed from a front of the earring safety device). The left and right flanges can extend from the rear guard towards the front guard and can be configured to restrict movement of an earring backing from lateral motion FIGS. 12-13 illustrate embodiments of an ear protection device using two different static spring designs. In these embodiments, front and rear guards 402, 404 are connected to form a single component via a "static spring." The static spring can comprise any connecting material that causes the front and rear guards 402, 404 to be biased toward each other via rotation about an axis proximal to the static spring. In some instances, the static spring can be formed from a different material than the front and rear guards 402, 404.

Figure 14:
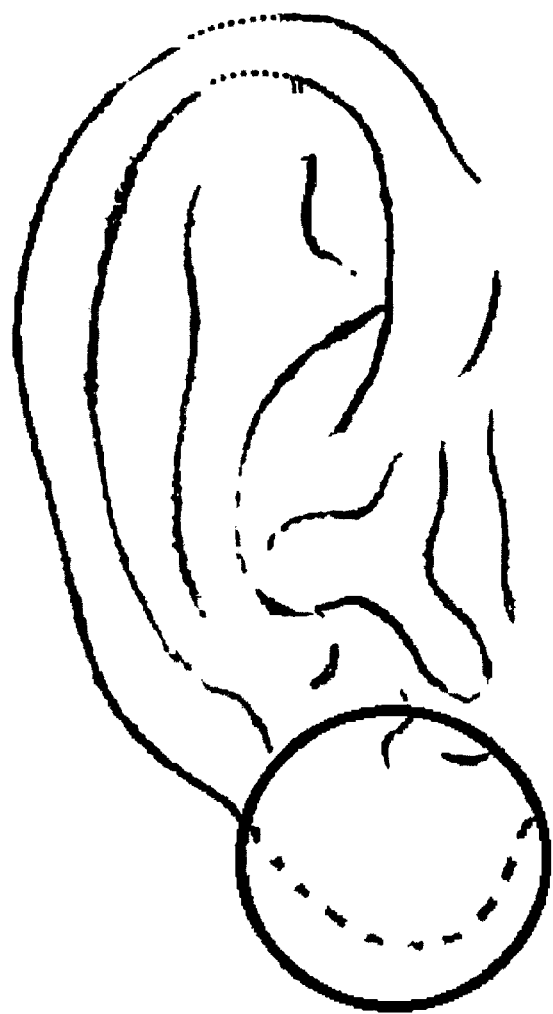
FIG. 14 illustrates an embodiment of an ear protection device using a rubber guard or slot design.

FIG. 14 illustrates an embodiment of an ear protection device using a rubber guard or slot design. This embodiment involves a single component (e.g., rubber component) shaped to fit over an earring and including a slot whereby the ear protection device can be fitted over the earring. The rubber guard or slot design can be formed from a flexible material such as rubber so that the device is malleable and the slot can be opened to enable entry and exit of the earring. A back of the rubber guard or slot design can include an extension designed to hold a post and backing of the earring. The slot can be opened via squeezing of the device and then returns to a closed position when the squeezing force is removed. The device is design to slide up and over an earlobe and earring.

Figure 15:
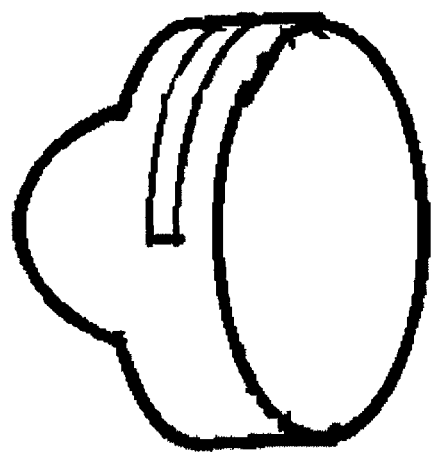
FIG. 15 illustrates a head on view of the rubber guard or slotted design as engaged on an earlobe and covering an earring.

FIG. 15 illustrates a head on view of the rubber guard or slotted design as engaged on an earlobe and covering an earring.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An earring safety device arranged over an earring of an ear comprising:
   a front guard configured for proximal arrangement to a front of an earring so as to protect the earring from external contact, the front guard arranged so as to hook around an antitragus or helix of an ear and assist in holding the earring safety device onto the ear, the front guard being tapered such that a bottom of the front guard is wider than a top of the front guard;
   a rear guard pivotally coupled to the front guard,
   a camming lobe of the rear guard shaped to provide a first resistance to rotation of the front and rear guards relative to each other when the front and rear guards are rotated between open and closed positions, and to provide at least a second resistance to rotation of the front and rear guards relative to each other when the front and rear guards are in the open or closed positions, the first resistance being greater than the second resistance;
   right and left flanges of the rear guard extending from the rear guard towards the front guard and configured to restrict movement of an earring backing of the earring from lateral motion.

2. The earring safety device of claim 1, further comprising an earring release slot in the rear guard.

3. The earring safety device of claim 1, wherein the rear guard is tapered such that a bottom of the rear guard is wider than a top of the rear guard.

4. The earring safety device of claim 1, wherein the rear guard is concave.

5. The earring safety device of claim 4, wherein rear guard and the right and left flanges form a concave region configured to at least partially surround the earring backing of the earring.

6. The earring safety device of claim 5, wherein the concave region is configured to accept an earring backing of a second earring having a different shape than the backing of the first earring.

7. The earring safety device of claim 1, wherein the earring is fixed to an earlobe of an ear.

8. The earring safety device of claim 1, wherein the earring is fixed to a helix of an ear.

9. The earring safety device of claim 1, wherein the front guard includes a top curved portion configured to hook around an antitragus or helix of an ear and assist in holding the earring safety device onto the ear.

10. An earring safety device arranged over an earring of an ear comprising:
    a front guard configured for proximal arrangement to a front of an earring so as to protect the earring from external impacts, a top curved portion of the front guard arranged so as to hook around an antitragus or helix of the ear and assist in holding the earring safety device onto the ear;
    a rear guard pivotally coupled to the front guard;
    the front guard being tapered such that a bottom of the front guard is wider than a top of the front guard; and a camming lobe of the rear guard shaped to provide a first resistance to rotation of the front and rear guards relative to each other when the front and rear guards are rotated between open and closed positions, and to provide at least a second resistance to rotation of the front and rear guards relative to each other when the front and rear guards are in the open or closed positions, the first resistance being greater than the second resistance.

11. The earring safety device of claim 10, wherein the front guard is configured to hook around an antitragus or helix of an ear and assist in holding the earring safety device onto the ear.

12. The earring safety device of claim 10, the rear guard further comprising right and left flanges extending towards the front guard and configured to restrict movement of an earring backing from lateral motion.

13. The earring safety device of claim 12, wherein the front guard provides a first side of protection to an earring, the rear guard provides second, third, and fourth sides of protection to the earring, and the right and left flanges provide fifth and sixth sides of protection to the earring.

14. The earring safety device of claim 10, wherein the front guard and rear guard each comprise a pair of tabs, the tabs arranged to interface the front and rear guards.

15. The earring safety device of claim 14, wherein the pair of tabs of the front guard interface with the camming lobe to provide the first resistance and at least the second resistance.

16. The earring safety device of claim 10, wherein the front guard is made from a material having a first hardness, and wherein a portion of a surface of the front guard includes a layer made of a second material having a second hardness that is softer than the first hardness.

17. The earring safety device of claim 10, wherein the rear guard is made from a material having a first hardness, and wherein a portion of a surface of the rear guard includes a layer made of a second material having a second hardness that is softer than the first hardness.

18. A method of protection against bodily harm from an earring fixed to an ear, the method comprising:
- rotatably separating a rear guard of an earring safety device from a front guard of the earring safety device creating a gap between a top of the rear guard and an inner surface of the front guard;
- fitting an edge of an earring and an edge of an ear that the earring is coupled to, through the gap so that the earring safety device envelopes the earring;
- rotating the front guard relative to the rear guard with sufficient force to overcome a friction or interference fit between the front guard and a camming lobe of the rear guard, thereby clamping the earring safety device to the edge of the ear in a closed position.

19. The method of claim 18, further comprising providing an earring release slot in the rear guard.

20. The method of claim 18, wherein the front guard is tapered such that a bottom of the front guard is wider than a top of the front guard.

* * * * *